(12) United States Patent
Madani et al.

(10) Patent No.: US 6,972,327 B1
(45) Date of Patent: Dec. 6, 2005

(54) REGENERATION OF CHROMATOGRAPHY MATERIAL

(75) Inventors: Hassan Madani, Seattle, WA (US); Robert D. Hershberg, Bainbridge Island, WA (US)

(73) Assignee: Immunex Corporation, Seattle, WA (US)

( * ) Notice: Subject to any disclaimer, the term of this patent is extended or adjusted under 35 U.S.C. 154(b) by 441 days.

(21) Appl. No.: 10/143,594

(22) Filed: May 8, 2002

Related U.S. Application Data

(60) Provisional application No. 60/289,697, filed on May 8, 2001, provisional application No. 60/325,801, filed on Sep. 28, 2001.

(51) Int. Cl.[7] .............................................. C07K 1/22
(52) U.S. Cl. ...................... 530/413; 210/670; 436/824; 436/828
(58) Field of Search ........................ 210/670; 530/413; 436/824, 828

(56) References Cited

U.S. PATENT DOCUMENTS

| | | | | |
|---|---|---|---|---|
| 5,242,802 A | * | 9/1993 | Berger et al. ................. | 435/7.9 |
| 5,268,306 A | * | 12/1993 | Berger et al. ................. | 436/527 |
| 5,962,291 A | * | 10/1999 | Graff et al. ............... | 435/188.5 |
| 6,080,696 A | | 6/2000 | Duke et al. .................... | 502/27 |
| 6,180,763 B1 | * | 1/2001 | Sherr et al. ................. | 530/413 |
| 6,531,579 B1 | * | 3/2003 | de Sauvage et al. ...... | 530/387.3 |
| 6,593,097 B1 | * | 7/2003 | Xu .............................. | 435/7.4 |

OTHER PUBLICATIONS

Allary et al., "Large scale production of human albumin: three years experience of an affinity chromatography process," *Bioseparation* 2(3):167-175, 1991.

Bill et al., "Optimization of protein G chromatography for biopharmaceutical monoclonal antibodies," *J. Mol. Recognit.* 8(1/2):90-94, 1995.

Cong et al., "Purification of recombinant human interferon-γ by immunoaffinity chromatography with monoclonal antibody," *Chin. J. Chem. Eng.* 3(3):125-133, 1995.

Desamaud et al., "Protein purification using combined streptavidin (or avidin)-Sepharose and thiopropyl-Sepharose affinity chromatography," *J. Chromatography* 603(1-2):95-104, 1992.

Fazekas et al, "Reusability of immunoaffinity columns for determination of fumonisins in maize," *Natural Toxins* 7(6): 259-263, 1999.

Fountoulakis et al., "Reduced binding capacity of concanavalin A-Sepharose after treatment with chaotropic agents," *J. Biochem. Biophys. Methods* 27(2):127-132, 1993.

Gagnon, *Purification Tools for Monoclonal Antibodies*, Validated Biosystems, Inc., Tucson, AZ, 1996, Ch. 9, "Protein A Affinity Chromatography," pp. 155-198.

Hale et al., "Repeated cleaning of protein A affinity column with sodium hydroxide," *J. Immunol. Methods* 171(1):15-21, 1994.

Sidhu, "A novel affinity purification of D-1 dopamine receptors from rat striatum," *J. Biol. Chem.* 265(17):10065-10072, 1990.

\* cited by examiner

*Primary Examiner*—David Saunders
(74) *Attorney, Agent, or Firm*—Kathleen Fowler

(57) ABSTRACT

The invention provides improved methods of regenerating and using affinity chromatography material, in particular Protein A affinity chromatography resins.

23 Claims, 1 Drawing Sheet

REGENERATION OF CHROMATOGRAPHY MATERIAL

RELATED APPLICATION DATA

This application claims the benefit of U.S. Provisional Applications 60/289,697, filed May 8, 2001, and 60/325,801, filed Sep. 28, 2001, the disclosures of which are incorporated by reference herein.

FIELD OF THE INVENTION

The invention is in the field of protein purification chromatography, particularly the use of affinity chromatography resins such as, for example, protein A chromatography resins.

BACKGROUND

Protein A affinity chromatography is frequently the method of choice to purify antibodies and other Fc-containing proteins (see "Purification Tools for Monoclonal Antibodies" by P. Gagnon, 1996, Validated Biosystems, Inc., Tucson, Ariz., Chapt. 9, Protein A Affinity Chromatography). A preparation containing antibodies is loaded onto a Protein A affinity chromatography resin, washed, and eluted, usually with either a low or high pH buffer. Purification as high as 95% in one step is possible (Id.).

The price of Protein A affinity chromatography resins is many times the cost of nonaffinity supports. In a commercial manufacturing process, this raw material cost can significantly add to the cost of goods (Id.). Protein A affinity chromatography resins can be recycled in order to reduce the cost of raw materials. Typically, Protein A affinity chromatography resins are recycled by treatment with strong chaotropic solutions (urea and guanidium HCl), or strongly acidic solutions (such as acetic acid), or a combination of the two. Guanidium HCl is more efficient at cleaning chromatography resins than urea, but in a large-scale production process presents disposal and environmental issues.

Eventually, as column performance degrades, the Protein A affinity chromatography resins are discarded and replaced. The invention provides methods of increasing the useful life and capacity of Protein A affinity chromatography resins, thereby reducing the costs of goods for protein manufacture.

SUMMARY OF THE INVENTION

The invention provides methods of regenerating chromatography resins by washing the chromatography resin with a chaotropic solution containing a reducing agent. Preferred chromatography resins are Protein A and Protein G affinity chromatography resins. The invention also entails using the regenerated resins to purify proteins of interest, particularly protein-based drugs.

DETAILED DESCRIPTION OF THE INVENTION

Figure 1:
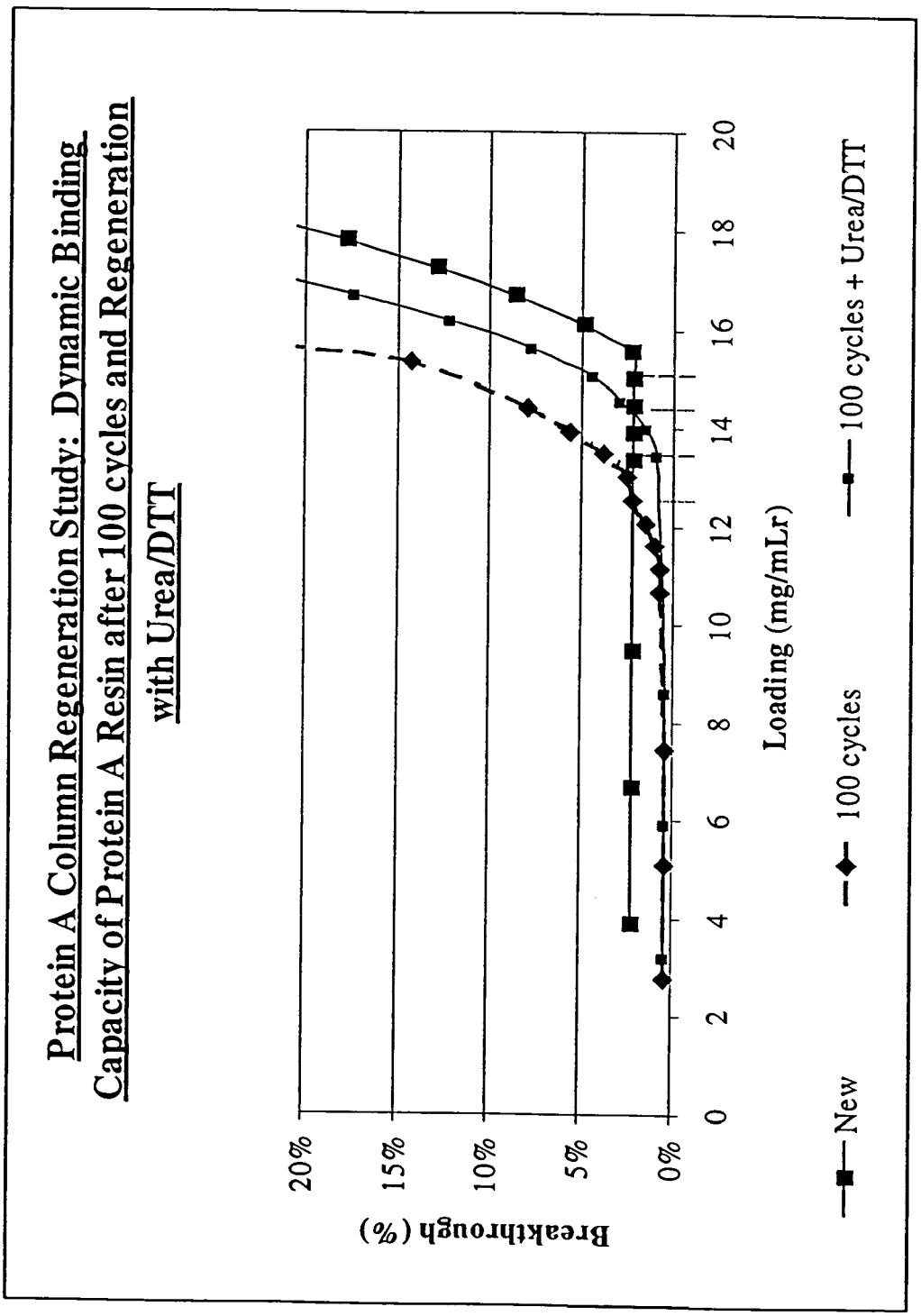
FIG. 1 is a graph of the binding capacity of Protein A resin when new (large squares), after 100 cycles (diamonds), and after 100 cycles with regeneration using urea/DTT as described in the example (small squares).

The invention provides a simple and environmentally tolerable method of more efficiently regenerating chromatography resins. In particular, the invention is useful for the regeneration of affinity column resins. Using the methods of the invention in a more efficient cleaning process results in increased lifetime of resin material. The more efficient regenerating methods of the invention permit extended performance of affinity resins for use in production of from gram to kilogram quantities of protein product.

In one aspect of the invention, there is provided a method of regenerating a Protein A or Protein G chromatography resin by washing the chromatography resin with a chaotropic solution containing a reducing agent. Chaotropic solutions that can be used in the methods of the invention include but are not limited urea and guanidium HCL. Preferably, the chaotropic agent in the chaotropic solution is at greater than about 200 mM, more preferably greater than about 500 mM, still more preferably greater than about 1 M, more preferably greater than about 2 M, more preferably greater than about 3 M, still more preferably greater than about 4 M, and even more preferably greater than about 5 M such as, for example, about 6 M. The reducing agent is a source of free thiols. Reducing agents that can be used include but are not limited to reduced glutathione, dithiothreitol (DTT), 2-mercaptoethanol, dithionitrobenzoate (DTNB), and cysteine. Preferably, the concentration of reducing agent in the chaotropic solution is at least about 1 mM, at least about 3 mM, preferably greater than about 5 mM, more preferably greater than about 10 mM, still more preferably greater than about 20 mM, still even more preferably greater than about 30 mM, and yet still even more preferably about 50 mM. The concentration of reducing agent can be even as high as 2 M, although usually around 50 mM is sufficient. In one working example of the method of the invention, a chaotropic solution is 6 M urea/50 mM DTT was found useful.

The column is typically washed with at least one column volume. The column can be washed with the chaotropic solution containing a reducing agent until no or essentially no protein further elutes from the column. Eluate from chromatography columns can be monitored by UV absorbence or by analysis of the eluate and/or resin by gel electrophoresis or any other method known to those of skill in the art.

Another aspect of the invention provides a method of eluting from a Protein A or Protein G chromatography resin an antibody or an Fc fusion protein that has been bound thereto, and regenerating the chromatography resin by washing the chromatography resin with a chaotropic solution containing a reducing agent. In another, related aspect, the invention provides a method of regenerating a Protein A or Protein G chromatography resin by washing the chromatography resin with a chaotropic solution containing a reducing agent, and then, after washing the column with an appropriate solution, re-using the clean chromatography resin for an additional round of purification. Accordingly, one can again bind an antibody or an Fc fusion protein to the Protein A or Protein G chromatography resin. In this aspect, the invention can further comprise eluting the antibody or the Fc fusion protein from the chromatography resin. Methods of eluting antibodies and Fc fusion proteins from such columns are well known in the art and include, for example, low pH or high pH elution conditions. In particular preferred embodiments, the antibody can be, for example, an antibody that immunospecifically recognize a human EGF receptor, a her-2/neu receptor, a CEA antigen, a Prostate Specific Membrane Antigen (PSMA), a CD5, a CD11a, a CD18, a NGF, a CD20, a CD25 (IL-2R, Tac), a CD33, a CD52, a GPIIbIIIa receptor, an Ep-cam, a TNF-alpha, a TGF-b1, a VEGF, an alpha 4 beta 7 integrin, an IgEs, a CMV protein. The Fc fusion protein can be an Fc domain covalently fused to a TNF receptor extracellular domain, a Flt3 ligand extracellular domain, or a RANK extracellular domain, to name just a few non-limiting examples.

It is expected that the methods of regenerating chromatography resins will be useful for other types of affinity resins besides Protein A and Protein G chromatography resins, particularly those affinity resins whose binding moieties do not contain disulfide bonds. For purposes of the invention, the term "affinity resins" excludes those resins that rely upon thiol binding such as glutathione resins for binding GST (glutathione S-transferase). Examples of affinity resins are avidin or streptavidin moieties, protein A, protein G, protein L, and sugar moiety resins (e.g., lectin chromatography resins). The inventive methods may also be used to regenerate ion exchange resins, size exclusion chromatography resins, and hydrophobic interaction chromatography resins, particularly on an industrial scale. By "industrial scale" is meant that the volume of chromatography resin used is at least about 1 liter, more preferably about 3 liters, still more preferably about 6 liters, even more preferably about 10 liters, still even more preferably about 50 liters, yet even more preferably about 100 liters. In fact, the volume of chromatography resin used together in industrial scale processes can be as large as 300 to 500 liters.

The methods of the invention can potentially be used in the purification of just about any protein, and is particularly advantageous for proteins that bind to affinity resins such as, for example, protein A and/or protein G. A protein is generally understood to be a polypeptide of at least about 10 amino acids, more preferably at least about 25 amino acids, even more preferably at least about 75 amino acids, and most preferably at least about 100 amino acids.

Generally, the methods of the invention are useful for in the purification of recombinant proteins. Recombinant proteins are proteins produced by the process of genetic engineering. The term "genetic engineering" refers to any recombinant DNA or RNA method used to create a host cell that expresses a gene at elevated levels, at lowered levels, or a mutant form of the gene. In other words, the cell has been transfected, transformed or transduced with a recombinant polynucleotide molecule, and thereby altered so as to cause the cell to alter expression of a desired protein. Methods and vectors for genetically engineering cells and/or cell lines to express a protein of interest are well known to those skilled in the art; for example, various techniques are illustrated in *Current Protocols in Molecular Biology*, Ausubel et al., eds. (Wiley & Sons, New York, 1988, and quarterly updates) and Sambrook et al., *Molecular Cloning: A Laboratory Manual* (Cold Spring Laboratory Press, 1989). Genetic engineering techniques include but are not limited to expression vectors, targeted homologous recombination and gene activation (see, for example, U.S. Pat. No. 5,272,071 to Chappel) and trans activation by engineered transcription factors (see, for example, Segal et al., 1999, Proc. Natl. Acad. Sci. USA 96(6):2758–63).

The proteins can be produced recombinantly in eukaryotic cells or prokaryotic cells. The proteins can be derived from genetically engineered plants, transgenic animals, or can be secreted by production cells adapted to grow in cell culture. Production cells can be bacterial (e.g., *E. coli, Streptomyces* spp., and *Bacillus* spp.), fungal (e.g., *Aspergillus*), invertebrate-derived (e.g., insect) or mammalian. Examples of mammalian cells commonly used in the industry are CHO, VERO, BHK, HeLa, CV 1 (including Cos), MDCK, 293, 3T3, myeloma cell lines (especially murine), PC12 and W138 cells. Particularly preferred host cells are Chinese hamster ovary (CHO) cells, which are widely used for the production of several complex recombinant proteins, e.g. cytokines, clotting factors, and antibodies (Brasel et al., 1996, Blood 88:2004–2012; Kaufman et al., 1988, J. Biol Chem 263: 6352–6362; McKinnon et al., 1991, J Mol Endocrinol 6:231–239; Wood et al., 1990, J. Immunol 145:3011–3016). The dihydrofolate reductase (DHFR)-deficient mutant cell line (Urlaub et al., 1980, Proc Natl Acad Sci USA 77:4216–4220), DXB11 and DG-44, are the CHO host cell lines of choice because the efficient DHFR selectable and amplifiable gene expression system allows high level recombinant protein expression in these cells (Kaufman R. J., 1990, Meth Enzymol 185:527–566). In addition, these cells are easy to manipulate as adherent or suspension cultures and exhibit relatively good genetic stability. CHO cells and recombinant proteins expressed in them have been extensively characterized and have been approved for use in clinical manufacturing by regulatory agencies.

Particularly preferred proteins are protein-based drugs, also known as biologics. Preferably, the proteins are expressed as extracellular products. Proteins that can be purified using the methods of the invention include but are not limited to a Flt3 ligand, a CD40 ligand, erythropoeitin, thrombopoeitin, calcitonin, Fas ligand, ligand for receptor activator of NF-kappa B (RANKL), TNF-related apoptosis-inducing ligand (TRAIL), ORK/Tek, thymic stroma-derived lymphopoietin, granulocyte colony stimulating factor, granulocyte-macrophage colony stimulating factor, mast cell growth factor, stem cell growth factor, epidermal growth factor, RANTES, growth hormone, insulin, insulinotropin, insulin-like growth factors, parathyroid hormone, interferons, nerve growth factors, glucagon, interleukins 1 through 18, colony stimulating factors, lymphotoxin-$\beta$, tumor necrosis factor, leukemia inhibitory factor, oncostatin-M, and various ligands for cell surface molecules Elk and Hek (such as the ligands for eph-related kinases, or LERKS). Descriptions of proteins that can be produced according to the inventive methods may be found in, for example, *Human Cytokines: Handbook for Basic and Clinical Research, Vol. II* (Aggarwal and Gutterman, eds. Blackwell Sciences, Cambridge Mass., 1998); *Growth Factors: A Practical Approach* (McKay and Leigh, eds., Oxford University Press Inc., New York, 1993) and *The Cytokine Handbook* (A W Thompson, ed.; Academic Press, San Diego Calif.; 1991).

Purification of the receptors for any of the aforementioned proteins can also be improved using the inventive methods, including the receptors for both forms of tumor necrosis factor receptor (referred to as p55 and p75), Interleukin-1 receptors (type 1 and 2), Interleukin-4 receptor, Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK), receptors for TRAIL, and receptors that comprise death domains, such as Fas or Apoptosis-Inducing Receptor (AIR). A particularly preferred receptor is a soluble form of the IL-1 receptor type II; such proteins are described in U.S. Pat. No. 5,767,064, incorporated herein by reference in its entirety.

Other proteins that can be produced using the inventive methods include cluster of differentiation antigens (referred to as CD proteins), for example, those disclosed in *Leuko-* cyte Typing VI (*Proceedings of the VIth International Workshop and Conference*; Kishimoto, Kikutani et al., eds.; Kobe, Japan, 1996), or CD molecules disclosed in subsequent workshops. Examples of such molecules include CD27, CD30, CD39, CD40; and ligands thereto (CD27 ligand, CD30 ligand and CD40 ligand). Several of these are members of the TNF receptor family, which also includes 41BB and OX40; the ligands are often members of the TNF family (as are 41BB ligand and OX40 ligand); accordingly, members of the TNF and TNFR families can also be produced using the present invention.

Proteins that are enzymatically active can also be purified according to the instant invention. Examples include metalloproteinase-disintegrin family members, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, and numerous other enzymes. Ligands for enzymatically active proteins can also be produced by applying the instant invention.

Various fusion proteins can also be produced using the inventive methods. Examples of such fusion proteins include proteins expressed as a fusion with a portion of an immunoglobulin molecule, proteins expressed as fusion proteins with a zipper moiety, and novel polyfunctional proteins such as a fusion proteins of a cytokine and a growth factor (i.e., GM-CSF and IL-3, MGF and IL-3). Any of the above-enumerated molecules can be expressed as a fusion protein including but not limited to the extracellular domain of a cellular receptor molecule, an enzyme, a hormone, a cytokine, a portion of an immunoglobulin molecule, a zipper domain, and an epitope. A particularly preferred fusion protein is the TNF-R:Fc fusion described in, for example, U.S. Pat. No. 5,605,690, and particularly the TNF-R:Fc that is commercially available as ENBREL® (etanercept).

Generally, the inventive methods are useful for purification of proteins that bind to protein A and/or protein G resins. Such proteins include fusions of any of the above-enumerated molecules to a constant region portion of an antibody, immunoglobulin molecules or portions thereof, and chimeric antibodies (i.e., an antibody having a human constant region couples to a murine antigen binding region) or fragments thereof. Numerous techniques are known by which DNA encoding immunoglobulin molecules can be manipulated to yield DNAs capable of encoding recombinant proteins such as single chain antibodies, antibodies with enhanced affinity, or other antibody-based polypeptides (see, for example, Larrick et al., 1989, Biotechnology 7:934–938; Reichmann et al., 1988, Nature 332:323–327; Roberts et al., 1987, Nature 328:731–734; Verhoeyen et al., 1988, Science 239:1534–1536; Chaudhary et al., 1989, Nature 339:394–397). Preparations of fully human antibodies (such as are prepared using transgenic animals, and optionally further modified in vitro), as well as humanized antibodies, can also be used in the invention. The term humanized antibody also encompasses single chain antibodies. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al.. EP 0 519 596 A1. For example, the invention can be used to in processes for the purification of human and/or humanized antibodies that immunospecifically recognize specific cellular targets, e.g., the human EGF receptor, the her-2/neu receptor, the CEA antigen, Prostate Specific Membrane Antigen (PSMA), CD5, CD11a, CD18, NGF, CD20, CD25 (IL-2R, Tac), CD33, CD52, GPIIbIIIa receptor, Ep-cam, other cancer cell surface molecules, TNF-alpha, TGF-b1, VEGF, other cytokines, alpha 4 beta 7 integrin, IgE, viral proteins (for example, cytomegalovirus and RSV), etc., to name just a few.

The resulting expressed polypeptide can then be purified, or partially purified, from such culture or component (e.g., from culture medium or cell extracts or bodily fluid) using known processes in combination with the methods of the invention. By "partially purified" means that some fractionation procedure, or procedures, have been carried out, but that more polypeptide species (at least 10%) than the desired protein is present. By "purified" is meant that the protein is essentially homogeneous, i.e., less than 1% contaminating proteins are present. Fractionation procedures can include but are not limited to one or more steps of filtration, centrifugation, precipitation, phase separation, affinity purification, gel filtration, ion exchange chromatography, hydrophobic interaction chromatography (HIC; using such resins as phenyl ether, butyl ether, or propyl ether), HPLC, or some combination of above. Any of the above chromatography resins can be regenerated using the methods of the invention.

For example, in a preferred aspect of the invention, the affinity purification steps can involve a Protein A or a Protein G affinity chromatography step, which affinity agents bind to proteins that contain Fc domains. Polypeptides can be removed from an affinity column using conventional techniques, e.g., in a high salt elution buffer and then dialyzed into a lower salt buffer for use or by changing pH or other components depending on the affinity matrix utilized, or can be competitively removed using the naturally occurring substrate of the affinity moiety. The Protein A or Protein G affinity chromatography resin is then regenerated using a combination of a chaotropic agent and a reducing agent, as herein described. After regeneration, the resin can be used for another purification cycle.

The desired degree of final purity depends on the intended use of the polypeptide. A relatively high degree of purity is desired when the polypeptide is to be administered in vivo, for example. In such a case, the polypeptides are purified such that no polypeptide bands corresponding to other polypeptides are detectable upon analysis by SDS-polyacrylamide gel electrophoresis (SDS-PAGE). It will be recognized by one skilled in the pertinent field that multiple bands corresponding to the polypeptide can be visualized by SDS-PAGE, due to differential glycosylation, differential post-translational processing, and the like. Most preferably, the polypeptide of the invention is purified to substantial homogeneity, as indicated by a single polypeptide band upon analysis by SDS-PAGE. The polypeptide band can be visualized by silver staining, Coomassie blue staining, or (if the polypeptide is radiolabeled) by autoradiography.

The invention also optionally encompasses further formulating the proteins. By the term "formulating" is meant that a protein can be buffer exchanged, and/or stored and/or further processed to a sterile dosage form. For purposes of the invention, the term "sterile bulk form" means that a formulation is free, or essentially free, of microbial contamination (to such an extent as is acceptable for food and/or drug purposes), and is of defined composition and concentration. The term "sterile unit dose form" means a form that is appropriate for the customer and/or patient administration or consumption. Such compositions can comprise an effective amount of the protein, in combination with other components such as a physiologically acceptable diluent, carrier, or excipient. The term "pharmaceutically acceptable" means a non-toxic material that does not interfere with the effectiveness of the biological activity of the active ingredient(s).

Formulations suitable for administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in *Remington's Pharmaceutical Sciences,* 16th ed. 1980, Mack Publishing Company, Easton, Pa. In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323. Such compositions will influence the physical state, solubility, stability, rate of in vivo release, and rate of in vivo clearance, and are thus chosen according to the intended application, so that the characteristics of the carrier will depend on the selected route of administration. Sustained-release forms suitable for use include, but are not limited to, polypeptides that are encapsulated in a slowly-dissolving biocompatible polymer (such as the alginate microparticles described in U.S. Pat. No. 6,036,978), admixed with such a polymer (including topically applied hydrogels), and or encased in a biocompatible semi-permeable implant.

The invention having been described, the following example is offered by way of illustration, and not limitation.

EXAMPLE

Regeneration of Protein A Chromatography Resin

Protein A chromatography resin (Sepharose FF Protein A, Pharmacia) was used to purify an Fc fusion protein in a manufacturing procedure for approximately 100 cycles. The initial capacity of the resin for the Fc fusion protein was 16.8 mgs protein per ml of resin. Between each cycle, the resin was cleaned with 1 column volume of 6 M urea, and 2 column volumes of 1 M acetic acid (pH 2.5). After 100 cycles, the measured capacity of the resin was 14.7 mgs per ml. Additional cleaning with 6 M urea or 1 M acetic acid did not improve capacity.

The resin was then cleaned w/6 M urea containing 50 mM DTT (pH 7 to 8) for approximately 2 column volumes, or until no protein was detectable in the flow through using UV absorbance. The capacity of the newly regenerated column was measured, and found to have increased to 15.9 mgs protein per ml of resin. These results are presented graphically in FIG. 1. Furthermore, residual contaminants (extracted using SDS) that were still bound to the resin after the Urea/DTT and Guanidine/DTT were significantly reduced post treatment as compared to in the absence of added reducing agent. Thus, the addition of reducing agent to the column regeneration process resulted in significantly more efficient cleaning and greater capacity. Adoption of this procedure on a large manufacturing scale will lead to improved column performance, increased column lifetime, and lower raw material cost.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method comprising
   eluting from a Protein A or Protein G chromatography resin an antibody or an Fc fusion protein that has been bound thereto, and
   regenerating the chromatography resin by washing the chromatography resin with a chaotropic solution containing a reducing agent.

2. The method of claim 1 wherein the Fc fusion protein comprises a polypeptide selected from the group consisting of a TNF receptor extracellular domain, a Flt3 ligand extracellular domain, and a RANK extracellular domain.

3. The method of claim 1 wherein the antibody immunospecifically recognizes an antigen selected from the group consisting of a human EGF receptor, a her-2/neu receptor, a CEA antigen, a Prostate Specific Membrane Antigen (PSMA), a CD5, a CD11a, a CD18, a NGF, a CD20, a CD25 (IL-2R, Tac), a CD33, a CD52, a GPIIbIIIa receptor, an Ep-cam, a TNF-alpha, a TGF-b1, a VEGF, an alpha 4 beta 7 integrin, an IgE, and a CMV protein.

4. The method of claim 1 wherein the chaotropic solution is 6 M urea.

5. The method of claim 4 wherein the antibody immunospecifically recognizes an antigen selected from the group consisting of a human EGF receptor, a her-2/neu receptor, a CEA antigen, a Prostate Specific Membrane Antigen (PSMA), a CD5, a CD11a, a CD18, a NGF, a CD20, a CD25 (IL-2R, Tac), a CD33, a CD52, a GPIIbIIIa receptor, an Ep-cam, a TNF-alpha, a TGF-b 1, a VEGF, an alpha 4 beta 7 integrin, an IgE, and a CMV protein.

6. The method of claim 4 wherein the Fc fusion protein comprises a polypeptide selected from the group consisting of a TNF receptor extracellular domain, a Flt3 ligand extracellular domain, and a RANK extracellular domain.

7. The method of claim 4, wherein the reducing agent is 50 mM DTT.

8. A method for regenerating a Protein A or Protein G chromatography resin comprising
   washing the chromatography resin with a chaotropic solution containing a reducing agent, and
   binding an antibody or an Fc fusion protein to the washed chromatography resin.

9. The method of claim 8 wherein the antibody immunospecifically recognizes an antigen selected from the group consisting of a human EGF receptor, a her-2/neu receptor, a CEA antigen, a Prostate Specific Membrane Antigen (PSMA), a CD5, a CD11a, a CD18, a NGF, a CD20, a CD25 (IL-2R, Tac), a CD33, a CD52, a GPIIbIIIa receptor, an Ep-cam, a TNF-alpha, a TGF-b1, a VEGF, an alpha 4 beta 7 integrin, an IgE, and a CMV protein.

10. The method of claim 8 wherein the Fc fusion protein comprises a polypeptide selected from the group consisting of a TNF receptor extracellular domain, a Flt3 ligand extracellular domain, and a RANK extracellular domain.

11. The method of claim 8, further comprising eluting the antibody or the Fc fusion protein from the chromatography resin.

12. The method of claim 11, further comprising formulating the antibody or the Fc fusion protein in a sterile bulk form.

13. The method of claim 12 wherein the antibody immunospecifically recognizes an antigen selected from the group consisting of a human EGF receptor, a her-2/neu receptor, a CEA antigen, a Prostate Specific Membrane Antigen (PSMA), a CD5, a CD11a, a CD18, a NGF, a CD20, a CD25 (IL-2R, Tac), a CD33, a CD52, a GPIIbIIIa receptor, an Ep-cam, a TNF-alpha, a TGF-b1, a VEGF, an alpha 4 beta 7 integrin, an IgE, and a CMV protein.

14. The method of claim 12 wherein the Fc fusion protein comprises a polypeptide selected from the group consisting of a TNF receptor extracellular domain, a Flt3 ligand extracellular domain, and a RANK extracellular domain.

15. The method of claim 11 wherein the antibody immunospecifically recognizes an antigen selected from the group consisting of a human EGF receptor, a her-2/neu receptor, a CEA antigen, a Prostate Specific Membrane Antigen (PSMA), a CD5, a CD11a, a CD18, a NGF, a CD20, a CD25 (IL-2R, Tac), a CD33, a CD52, a GPIIbIIIa receptor, an Ep-cam, a TNF-alpha, a TGF-b 1, a VEGF, an alpha 4 beta 7 integrin, an IgE, and a CMV protein.

16. The method of claim 11 wherein the Fc fusion protein comprises a polypeptide selected from the group consisting of a TNF receptor extracellular domain, a Flt3 ligand extracellular domain, and a RANK extracellular domain.

17. The method of claim 8 wherein the chaotropic solution is 6 M urea.

18. The method of claim 17 wherein the Fc fusion protein comprises a polypeptide selected from the group consisting of a TNF receptor extracellular domain, a Flt3 ligand extracellular domain, and a RANK extracellular domain.

19. The method of claim 17 wherein the antibody immunospecifically recognizes an antigen selected from the group consisting of a human EGF receptor, a her-2/neu receptor, a CEA antigen, a Prostate Specific Membrane Antigen (PSMA), a CD5, a CD11a, a CD18, a NGF, a CD20, a CD25 (IL-2R, Tac), a CD33, a CD52, a GPIIbIIIa receptor, an Ep-cam, a TNF-alpha, a TGF-b1, a VEGF, an alpha 4 beta 7 integrin, an IgE, and a CMV protein.

20. The method of claim 17, wherein the reducing agent is 50 mM DTT.

21. A method of regenerating a column of Protein A or Protein G chromatography resin, comprising washing the column of chromatography resin with a chaotropic solution containing a reducing agent, thereby regenerating the column.

22. The method of claim 21 wherein the chaotropic solution is 6 M urea.

23. The method of claim 22, wherein the reducing agent is 50 mM DTT.

* * * * *